United States Patent
Cowell et al.

(10) Patent No.: US 7,388,123 B2
(45) Date of Patent: Jun. 17, 2008

(54) FEMININE CARE ABSORBENT ARTICLES HAVING GUIDES FOR IMPROVED FLUID HANDLING

(75) Inventors: Christine M. Cowell, Fond du Lac, WI (US); Teresa D. Petryk, Woodstock, GA (US); Patricia A. Stern, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 378 days.

(21) Appl. No.: 10/334,159

(22) Filed: Dec. 30, 2002

(65) Prior Publication Data
US 2004/0127883 A1   Jul. 1, 2004

(51) Int. Cl.
*A61F 13/513* (2006.01)
(52) U.S. Cl. ...................... 604/382; 424/402
(58) Field of Classification Search ................ 604/378, 604/385, 358, 364, 380, 361, 381, 382, 385.24; 156/73.1; 264/254; 424/402
See application file for complete search history.

(56) References Cited

U.S. PATENT DOCUMENTS

| | | | | |
|---|---|---|---|---|
| 3,371,668 A | * | 3/1968 | Johnson | 604/366 |
| 3,489,148 A | * | 1/1970 | Duncan et al. | 604/382 |
| 3,902,493 A | * | 9/1975 | Baier et al. | 604/286 |
| 4,015,604 A | * | 4/1977 | Csillag | 604/382 |
| 4,623,340 A | | 11/1986 | Luceri | |
| 4,684,956 A | | 8/1987 | Ball | |
| 4,718,898 A | | 1/1988 | Puletti et al. | |
| 4,758,276 A | | 7/1988 | Lin et al. | |
| 4,762,520 A | | 8/1988 | Wallstrom | |
| 4,778,458 A | | 10/1988 | Gronostajski | |
| 4,848,572 A | * | 7/1989 | Herrera | 206/440 |
| 4,892,536 A | * | 1/1990 | DesMarais et al. | 604/385.27 |
| 5,037,415 A | * | 8/1991 | Leroy et al. | 604/385.25 |
| 5,100,398 A | * | 3/1992 | Leroy et al. | 604/385.25 |
| 5,312,386 A | * | 5/1994 | Correa et al. | 604/379 |

(Continued)

FOREIGN PATENT DOCUMENTS

DE        19603840        8/1997

(Continued)

OTHER PUBLICATIONS

U.S. Appl. No. 09/991,185, filed Nov. 16, 2001.

(Continued)

*Primary Examiner*—Tatyana Zalukaeva
*Assistant Examiner*—Paula L Craig
(74) *Attorney, Agent, or Firm*—Dority & Manning, P.A.

(57) ABSTRACT

An absorbent article, such as a feminine care product, includes a liquid permeable top cover, a generally liquid impermeable outer cover, and an absorbent structure disposed between the top cover and outer cover. A band of spaced apart deposits of a barrier substance material, such as a phase-change liquid, are defined on the top cover (inner or outer surface) along a portion of opposite lateral sides of the article. The deposits have a desired height of topography with respect to a surface of the top cover. The deposits are defined such that areas of the top cover are exposed within the band, the band thereby being permeable to bodily fluids insulting the article within the band or from above the band while acting as a fluid barrier against lateral flow of bodily fluids across the band.

16 Claims, 4 Drawing Sheets

U.S. PATENT DOCUMENTS

| | | | | |
|---|---|---|---|---|
| 5,342,343 | A * | 8/1994 | Kitaoka et al. | 604/385.29 |
| 5,431,643 | A * | 7/1995 | Ouellette et al. | 604/385.05 |
| 5,439,458 | A * | 8/1995 | Noel et al. | 604/378 |
| 5,454,801 | A | 10/1995 | Lauritzen | |
| 5,533,991 | A | 7/1996 | Kirby et al. | |
| 5,613,962 | A | 3/1997 | Kenmochi et al. | |
| 5,620,742 | A | 4/1997 | Lauritzen | |
| 5,713,885 | A * | 2/1998 | Jorgenson et al. | 604/385.201 |
| 5,762,642 | A | 6/1998 | Coles et al. | |
| 5,797,895 | A * | 8/1998 | Widlund et al. | 604/385.24 |
| 5,803,920 | A * | 9/1998 | Gilman | 604/378 |
| 5,807,365 | A * | 9/1998 | Luceri | 604/367 |
| 5,807,367 | A | 9/1998 | Dilnik et al. | |
| 5,834,114 | A | 11/1998 | Economy et al. | |
| 5,931,823 | A * | 8/1999 | Stokes et al. | 604/358 |
| 5,938,826 | A | 8/1999 | Baker et al. | |
| 6,013,066 | A | 1/2000 | Samuelsson | |
| 6,015,936 | A * | 1/2000 | Takai et al. | 604/383 |
| 6,120,783 | A * | 9/2000 | Roe et al. | 424/402 |
| 6,140,551 | A | 10/2000 | Niemeyer et al. | |
| 6,149,934 | A * | 11/2000 | Krzysik et al. | 424/443 |
| 6,258,997 | B1 | 7/2001 | Johansson et al. | |
| 6,365,794 | B1 | 4/2002 | Dabi et al. | |
| 6,376,741 | B1 | 4/2002 | Guarracino et al. | |
| 6,395,957 | B1 | 5/2002 | Chen et al. | |
| 6,413,338 | B1 * | 7/2002 | DiPalma | 156/73.1 |
| 6,417,426 | B1 | 7/2002 | Takai et al. | |
| 6,436,328 | B1 * | 8/2002 | DiPalma | 264/254 |
| 6,440,111 | B1 | 8/2002 | Berba et al. | |
| 6,476,288 | B1 | 11/2002 | VanRijswijck et al. | |
| 6,479,728 | B1 * | 11/2002 | DiPalma | 604/378 |
| 6,506,961 | B1 * | 1/2003 | Levy | 604/380 |
| 6,525,239 | B2 * | 2/2003 | Cole | 604/382 |
| 6,528,698 | B2 * | 3/2003 | Mizutani et al. | 604/382 |
| 6,548,732 | B2 * | 4/2003 | Erdman et al. | 604/381 |
| 6,617,490 | B1 * | 9/2003 | Chen et al. | 604/380 |
| 6,642,427 | B2 * | 11/2003 | Roe et al. | 604/361 |
| 6,645,187 | B1 * | 11/2003 | DiPalma | 604/385.101 |
| 6,656,168 | B2 * | 12/2003 | Braverman et al. | 604/308 |
| 6,673,982 | B1 * | 1/2004 | Chen et al. | 604/378 |
| 6,934,969 | B2 * | 8/2005 | Schorr et al. | 2/51 |
| 6,939,553 | B2 * | 9/2005 | Yahiaoui et al. | 424/402 |
| 6,957,884 | B2 * | 10/2005 | Sharma et al. | 347/99 |
| 2001/0024716 | A1 | 9/2001 | Chen et al. | |
| 2002/0026165 | A1 * | 2/2002 | Elder et al. | 604/364 |
| 2002/0068917 | A1 | 6/2002 | VanGompel et al. | |
| 2002/0077618 | A1 | 6/2002 | Molas | |
| 2002/0087129 | A1 * | 7/2002 | Di Luccio et al. | 604/304 |
| 2002/0110689 | A1 | 8/2002 | Hu et al. | |
| 2002/0120249 | A1 * | 8/2002 | Wada et al. | 604/385.24 |
| 2002/0128615 | A1 | 9/2002 | Tyrrell et al. | |
| 2002/0138054 | A1 | 9/2002 | Erdman et al. | |
| 2004/0122386 | A1 * | 6/2004 | Mocadlo | 604/359 |
| 2004/0127872 | A1 * | 7/2004 | Petryk et al. | 604/382 |

FOREIGN PATENT DOCUMENTS

| | | |
|---|---|---|
| DE | 19816393 | 10/1999 |
| EP | 0140560 | 11/1988 |
| EP | 0392528 | 10/1990 |
| EP | 0526225 | 2/1993 |
| EP | 0604729 | 7/1994 |
| EP | 0748894 | 12/1996 |
| EP | 0698138 | 7/1999 |
| EP | 0951889 | 10/1999 |
| EP | 1099434 A1 | 5/2001 |
| EP | 0746296 | 6/2001 |
| EP | 1120097 | 8/2001 |
| EP | 1166732 | 1/2002 |
| GB | 807768 | 1/1959 |
| GB | 2284767 | 6/1995 |
| GB | 2308303 | 6/1997 |
| WO | 9319715 | 10/1993 |
| WO | 9836722 | 8/1998 |
| WO | 9915123 | 4/1999 |
| WO | 0145757 | 6/2001 |
| WO | 0197972 | 12/2001 |
| WO | 03013406 | 2/2003 |
| WO | 03043554 | 5/2003 |

OTHER PUBLICATIONS

U.S. Appl. No. 09/990,686, filed Nov. 16, 2001.
U.S. Appl. No. 10/328,338, filed Dec. 23, 2002.
EPO Search Report, Mar. 31, 2004.

* cited by examiner

FEMININE CARE ABSORBENT ARTICLES HAVING GUIDES FOR IMPROVED FLUID HANDLING

FIELD OF THE INVENTION

The present invention relates generally to the field of feminine care absorbent articles, and more particularly to a feminine care article having improved fluid handling properties.

BACKGROUND

Feminine care absorbent articles, such as sanitary napkins and pantiliners, typically include an absorbent structure enclosed between a body facing liquid permeable top cover and a liquid impermeable outer cover. The top cover and outer cover may extend laterally beyond the absorbent and be bonded together to form a peripheral seal around the article. The articles are positioned in the crotch portion of an undergarment for absorption of bodily exudates.

A concern with conventional feminine care articles is leakage of fluids when using the articles, particularly from around the side edges of the article. Such leakage may lead to embarrassment for the consumer and a general loss of confidence in use of the articles. Various attempts have been made in the art to incorporate structure in the articles to reduce or prevent leakage, including embossed walls or channels, polymeric or other liquid impermeable barrier walls, and the like. However, such attempts have not been completely successful at eliminating the leakage problem. Certain proposed solutions may even exacerbate the problem. For example, polymeric film barriers have been used along the side edges of feminine pads on each lateral side of a central insult area. However, due to any number of factors, including slippage of the product in use, relatively heavy menstrual flow, etc., there may often be times when menstrual fluid impacts or insults the pad on the film barriers. The fluid cannot permeate through the polymeric film barrier and is directed either towards the inboard insult area or to the side edges of the article thus resulting in leakage. Also, the fluid smears across the film barrier resulting in significant and potentially embarrassing staining of the article.

EP 0 746 296 B1 describes a sanitary napkin incorporating longitudinally directed barrier structures between the centerline of the product and each edge. The barrier structures are formed by a liquid impermeable substance, such as a wax, and may have the shape of a continuous line, or series of dots or dashes, disposed between the product centerline and longitudinal side edges. The width of the barrier structures is between 1 mm and 20 mm, particularly 3 mm. This type of barrier structure is relatively wide and acts as a dam to the laterally outward flow of fluid and requires a "safety margin" of absorbent core material between the structure and edges of the article.

Accordingly, the art is continually seeking methods and devices for improved leakage protection in feminine care articles, particularly sanitary napkins and panty liners.

SUMMARY

Objects and advantages of the invention will be set forth in part in the following description, or may be obvious from the description, or may be learned through practice of the invention.

In accordance with certain aspects of the invention, an absorbent article is provided with bands of a barrier substance material deposited on the top cover material along at least a portion of the periphery of the article. In a particular embodiment, the substance is a phase-change liquid. The band has a laterally inboard dimension generally overlying the absorbent structure and, in one embodiment, may have a laterally outboard dimension having the same general shape as the underlying absorbent structure so as to be generally coextensive with a periphery of the absorbent structure. In an alternate embodiment, the band may extend laterally outboard to the sealed edges of the article. The bands may be applied by any suitable technique, including inkjet printing, and are defined as a particular pattern of spaced apart deposits such that the band is permeable to bodily fluids within its boundaries while still defining a barrier topography to lateral flow of bodily fluids from the underlying absorbent or fluid that flows across the top cover before being absorbed by absorbent structure. Any number of deposit patterns may be employed so long as sufficient top cover material is exposed within the band for receipt of any fluid that may insult the article from generally above the band. For example, it may be desired that, within the dimensions of the band, between about 25% to about 75% of the surface area within the band is exposed top cover material. In a desired embodiment, about 30% to about 50% of the band area is exposed.

Although the present invention has particular usefulness for the field of feminine care articles, it should be appreciated that any manner of personal care absorbent article may benefit from the invention, including diapers, training pants, swim pants, incontinence articles, and the like. All such uses are within the scope and spirit of the invention. For ease of description only, the working environment of the invention is assumed to be feminine care sanitary napkins. The invention is not, however, limited to such use.

The deposit substance may be applied in various patterns within the band. In one particular embodiment of the invention, the deposit pattern may be defined by a series of continuous deposits of the substance, for example a band of relatively thin spaced apart stripes. For example, the band may have an overall width dimension overlying the absorbent structure of between about 5-20 mm, with each stripe having a width of about 0.25 mm. The stripes may be spaced apart from about 0.25 mm to about 0.75 mm. Various other continuous deposit patterns are also within the scope of the invention. The pattern of continuous stripes may be desired in that a continuous unbroken barrier is defined transverse to the direction of leakage. For example, if the band is defined as a longitudinally extending band along a lateral side margin to prevent leakage from the article sides, it may be desired that the band be generally continuous along the complete length thereof to prevent fluid from traveling along the band and then migrating through a space in the band pattern.

In alternate embodiments, the pattern of phase change liquid may be defined by a series of discontinuous deposits of the liquid, such as dashed lines, dots, or any other pattern providing sufficient exposed surface area of the top cover. A discontinuous or broken pattern may, under certain circumstances, prove beneficial in channeling bodily fluids to exposed top cover areas within the band. For example, the pattern may be broken, such as dashed lines, and define a tortuous path such that a straight or "unimpeded" path is not defined across the band. Any bodily fluid that migrates into the band through a space in the laterally inboard portion of the band cannot flow unimpeded across the band to the side of the article, but encounters other deposits of the barrier structure such that fluid is forced to change direction, preferably a number of times. The tortuous path slows the flow of fluid across the band and enables absorption of the fluid through the exposed areas of the top cover within the band.

Although the lateral sides of absorbent articles are typically the focus of leakage prevention efforts, it should be appreciated that leakage may also occur at the longitudinal ends of the articles. With the band configuration of the present invention, a barrier band of the deposit substance may be provided at any location around the periphery of the article, or around the entire periphery.

As mentioned, the deposit substance may be a phase-change liquid. Various embodiments of a phase-change liquid may be used in an ink-jet printing technique to define the barrier band. The liquid should be selected to ensure that it sufficiently adheres to the underlying top cover material. Exemplary phase-change liquids include, but are not limited to, waxes, petrolatum based lotions, adhesives, thermoplastics, and the like, and any combination thereof. For added benefits, the phase-change liquid may include a skin wellness agent, such as a medicant, emollient, ointment, moisturizer, and the like. For use in personal care absorbent articles, the use of skin-unfriendly components should be avoided.

It is desired that the phase-change liquid have sufficient viscosity and other properties such that upon solidifying, a deposit is formed having a desired height or topography with respect to the body-facing surface of the top cover, the band deposit thus providing desired fluid handling properties by forming a barrier "dam" and directional channel to a flow of bodily fluid. The topography may be carefully controlled by the parameters of the application technique.

It may be desired in certain embodiments that the deposit substance incorporate a highly visible color. In this manner, the deposit substance may be applied in a visible and pleasing aesthetic pattern.

Aspects of the invention will described below in greater detail by reference to particular embodiments, examples of which are illustrated in the figures.

DETAILED DESCRIPTION

Figure 1:
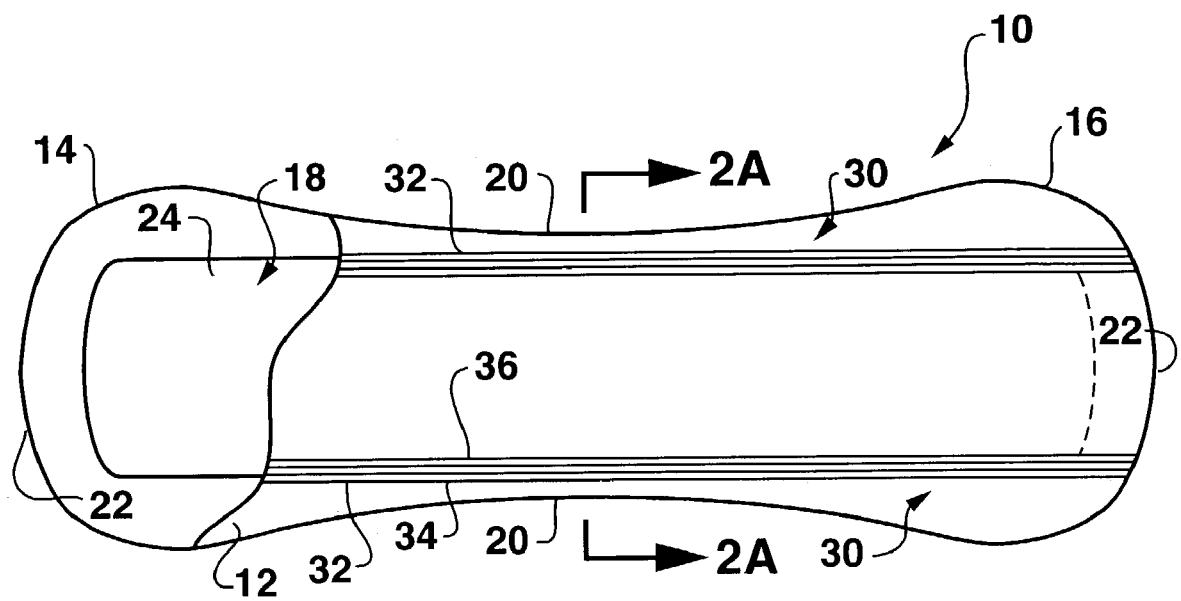
FIG. 1 is a perspective and partial cut-away of an absorbent article according to the invention.

The invention will now be described in detail with reference to particular embodiments thereof. The embodiments are provided by way of explanation of the invention, and are not meant as a limitation of the invention. For example, features described or illustrated as part of one embodiment may be used with another embodiment to yield still a further embodiment. It is intended that the present invention include these and other modifications and variations as come within the scope and spirit of the invention.

The present invention relates to any manner of absorbent article, such as diapers, training pants, swim pants, incontinence articles, feminine care articles, and the like. The construction and materials used in conventional absorbent articles vary widely and are well known to those of skill in the art. A detailed explanation of such materials and construction of conventional articles is not necessary for purposes of describing the present invention. The invention has particular usefulness for feminine care articles and, for purposes of illustration and description only, embodiments of feminine care articles according to the invention, in particular sanitary napkins, are referenced herein. However, it should be appreciated that the invention is in no way limited to sanitary napkins in particular, or to feminine care articles in general.

Referring to the figures in general, an absorbent article 10 according to the invention includes a generally liquid permeable top cover 12, a generally liquid impermeable outer cover 14, and an absorbent structure 18 disposed between the top cover 12 and outer cover 14. The top cover 12 and outer cover 14 are sealed together at their peripheral edges utilizing known techniques, such as, for example, gluing, crimping, hot-sealing or the like, the sealed edges defining an overall sealed peripheral edge 16 of the article 10. The article 10 may take on various but will generally have opposite lateral sides 20 and longitudinal ends 22. Various geometries of absorbent articles, including feminine care articles, are well known to those skilled in the art, and all such embodiments are within the scope and spirit of the invention.

The absorbent article 10 is desirably provided with sufficient capacity to absorb and retain the intended amount and type of bodily exudate(s). The absorbent capacity is provided by the fluid retentive absorbent structure 18. The absorbent structure 18 can be any structure or combination of components which are generally compressible, conformable, non-irritating to a wearer's skin, and capable of absorbing and retaining liquids and certain body wastes. For example, the structure 18 may include an absorbent web material 24 of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In a particular embodiment, the absorbent web material is a matrix of cellulosic fluff, and may also include superabsorbent hydrogel-forming particles. The cellulosic fluff may comprise a blend of wood pulp fluff. One preferred type of fluff is identified with the trade designation NB 416, available from Weyerhaeuser Corp., and is a bleached, highly absorbent wood pulp containing primarily soft wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. Methods and apparatus for carrying out such techniques are well known in the art.

As a general rule, the superabsorbent material is present in the absorbent web in an amount of from about 0 to about 90 weight percent based on total weight of the web. The web may have a density within the range of about 0.04 to about 0.35 grams per cubic centimeter. Superabsorbent materials are well known in the art and can be selected from natural, synthetic, and modified natural polymers and materials.

The absorbent web material may also be a coform material. The term "coform material" generally refers to composite materials comprising a mixture or stabilized matrix of thermoplastic fibers and a second non-thermoplastic material. Some examples of such coform materials are disclosed in U.S. Pat. Nos. 4,100,324 to Anderson, et al.; U.S. Pat. No. 5,284,703 to Everhart, et al.; and U.S. Pat. No. 5,350,624 to Georger, et al.; which are incorporated herein in their entirety by reference thereto for all purposes.

The absorbent web material utilized in the absorbent structure 18 is also selected so that the individual absorbent structure possesses a particular individual total absorbency depending on the intended article of use. For example, for infant care products, the total absorbency can be within the range of about 200-900 grams of 0.9 wt % saline, and can typically be about 500 g of saline. For adult care products, the total absorbency can be within the range of about 400-2000 grams of saline, and can typically be about 1300 g of saline. For feminine care products, the total absorbency can be within the range of about 7-50 grams of menstrual fluid, and can typically be within the range of about 30-40 g of menstrual fluid.

The absorbent structure 18 may be a multi-component and may include, for example, an intake layer or transfer delay layer in combination with the absorbent web 24. Such configurations are well known to those skilled in the art.

The fluid permeable top cover 12 has an outwardly facing surface that may contact the body of the wearer and receive bodily exudate(s). The top cover 12 desirably is made of a material which is flexible and non-irritating to the wearer. As used herein, the term "flexible" is intended to refer to materials which are compliant and readily conform to the bodily surface(s) with which such materials are in contact, or materials which respond by easily deforming in the presence of external forces.

The top cover 12 is provided for comfort and conformability and functions to direct bodily exudate(s) away from the body, through the top cover 12 and toward the absorbent structure 18. The top cover 12 should retain little or no liquid in its structure so that the cover provides a relatively comfortable and non-irritating surface next to the tissues within the vestibule of a female wearer. The top sheet 12 can be constructed of any woven or nonwoven material which is easily penetrated by bodily fluids which contact the surface of the cover. Examples of suitable cover materials include rayon, bonded carded webs of polyester, polypropylene, polyethylene, nylon, or other heat-bondable fibers, polyolefins, such as copolymers of polypropylene and polyethylene, linear low-density polyethylene, and aliphatic esters such as polylactic acid. Finely perforated film webs and net material can also be used. The cover may be apertured to increase its fluid intake capacity. A specific example of a suitable cover material is a bonded carded web made of polypropylene and polyethylene such as that used as cover stock for KOTEX® pantiliners and obtainable from Sandler Corporation, Germany. Other examples of suitable materials are composite materials of polymer and nonwoven fabric materials. The composite materials are typically in the form of integral sheets generally formed by the extrusion of a polymer onto a web of spunbonded material. The fluid permeable cover 12 can also contain a plurality of apertures formed therein which are intended to increase the rate at which bodily fluid(s) can penetrate through the cover and into the absorbent structure 18.

The top cover 12 may also be embossed with any desired embossing pattern to define embossed channels. Embossing techniques are well known to those skilled in the art. An embossing pattern not only creates an aesthetically pleasing surface, the channels facilitate intake of menses fluid. Menses will tend to flow along the densified edges of the channels rather than pool on contact points of the top cover 12.

The top cover 12 can be maintained in secured relation with the absorbent structure 18 by bonding all or a portion of the adjacent surfaces to one another. A variety of bonding methods known to one of skill in the art can be utilized to achieve any such secured relationship. Examples of such methods include, but are not limited to, the application of adhesives in a variety of patterns between the two adjoining surfaces, entangling at least portions of the adjacent surface of the absorbent with portions of the adjacent surface of the cover, or fusing at least portions of the adjacent surface of the cover to portions of the adjacent surface of the absorbent.

The back cover 14 may be any one of a number of suitable liquid impermeable materials known in the art for use as outer covers or baffles in absorbent articles. A specific example of a back cover material is a polyethylene film such as that used in KOTEX® pantiliners and obtainable from Pliant Corporation, Schaumburg, Ill., USA. The cover can be maintained in secured relation with the absorbent structure 18 by bonding all or a portion of the adjacent surfaces to one another. A variety of bonding methods known to one of skill in the art can be utilized to achieve any such secured relation. Examples of such methods include, but are not limited to, ultrasonic bonding, thermal bonding, or the application of adhesive materials in a variety of patterns between the two adjoining surfaces.

Figure 3:
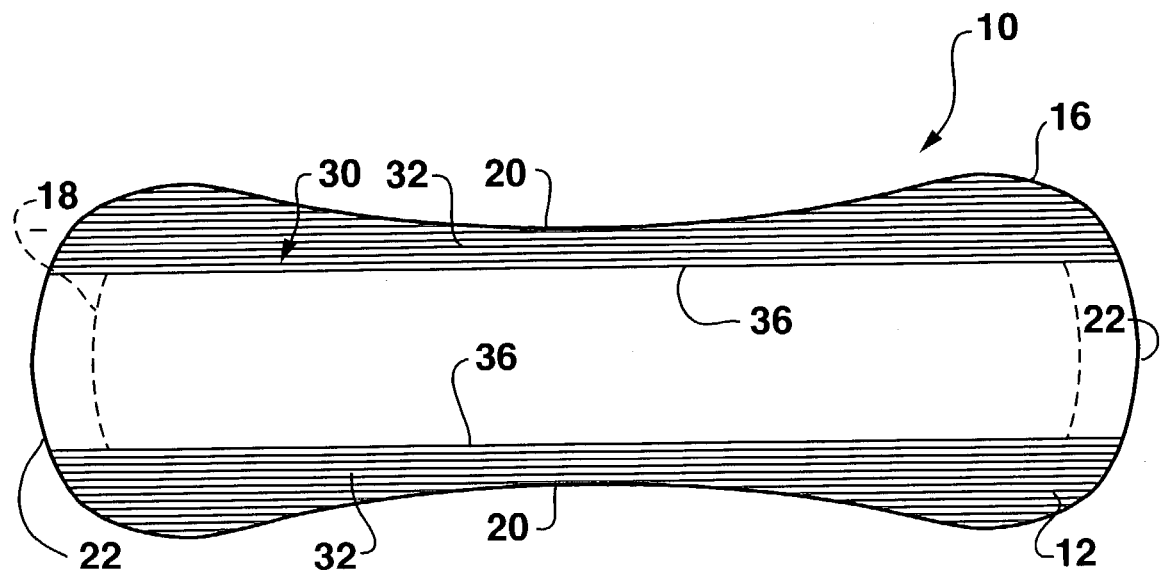
FIG. 3 is a top view of an alternate embodiment of an absorbent article according to the invention.

Referring to the figures in general, embodiments of the absorbent article 10 according to the invention include bands 30 of spaced apart deposits 32 of a barrier substance defined on the top cover 12. The bands 30 may be defined in a longitudinally extending pattern along opposite lateral sides of a longitudinal centerline of the article 10. At least a portion of each band 30 has a laterally inboard dimension 36 overlying a longitudinally extending periphery portion of the underlying absorbent structure 18. In certain embodiments for example as illustrated in FIGS. 1, 4, 5, and 6, the bands 30 include a laterally outboard deposit 34 that is spaced from the sealed peripheral edge 16 of the article 10. In other words, the bands 30 are defined as discrete bands having a generally uniform width along the article 10. This arrangement of the deposits 32 may be preferred from an aspect of conservation of the barrier substance. In alternate embodiments, for example as illustrated in FIGS. 3 and 7, the bands 30 may extend laterally outward to the sealed peripheral edge 16 of the article 10. This embodiment may be preferred from an ease of manufacturing standpoint, particularly where the bands 30 are printed on the top cover 12 prior to assembly of the respective components into the absorbent article 10.

Figure 2A:
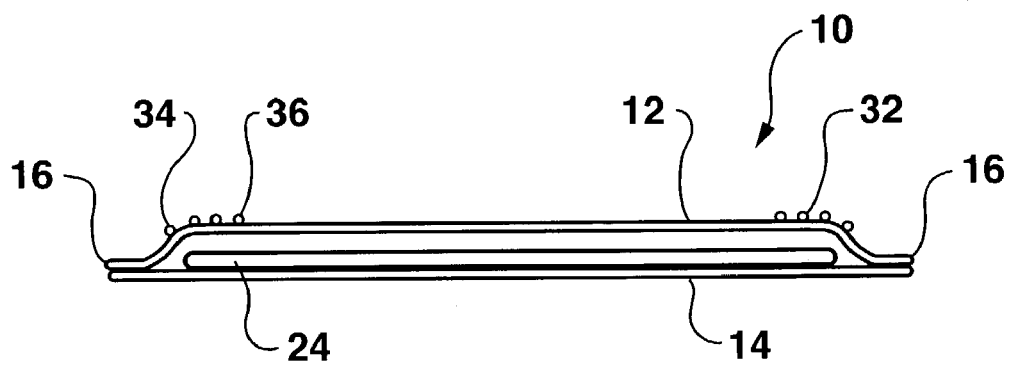
FIG. 2A is a cross-sectional view of the absorbent article taken along the lines indicated in FIG. 1.
Figure 2B:
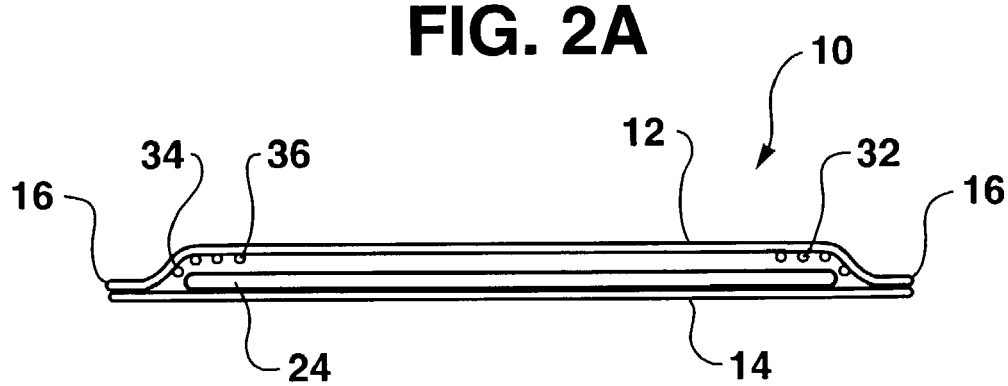
FIG. 2B is a cross-sectional view of an alternate embodiment of an absorbent article according to the invention.

It should be appreciated that the bands 30 may be provided on the body-facing surface of the top cover 12, as shown in FIG. 2A, or may be defined on the inner surface (facing the absorbent material 24) of the top cover 12, as shown in FIG. 2B.

With each of the different types of embodiments, between about 25% to about 75% of the surface area of the top cover 12 within the bands 30 is exposed (not covered or coated with the barrier substance). In this manner, a significant portion of the top cover material 12 and underlying absorbent structure 18 are available for absorption of bodily fluids that may be deposited onto the article 10 from the area above the bands 30, or that may flow over the laterally inboard deposits of the liquid.

A suitable group of barrier substances for use in the invention are phase-change liquids. As used herein, the term "phase-change" refers to a material which is processed in a liquid or substantially liquid state and then solidifies or returns to its natural state when cooled. Various phase-change liquids may be used with the present invention, for example such liquids may include, but are not limited to, medicaments, inks, waxes, paints, lotions, ointments, skin health agents, topical applications, or combinations thereof. In general, the phase-change liquid may be any application or composition which is capable of adhering or being applied to the top cover 12 so that, upon solidification, discrete barrier topographies are defined on the top cover 12. The material or composition is at least partially hydrophobic. The phase-change liquid may be, for example, a wax, petrolatum based lotion, adhesive, thermoplastic, and so forth. As used herein, the term "petrolatum" refers to a semi-solid mixture of hydrocarbons obtained from petroleum, such as Glenpure L white petrolatum available from Glen Corporation of St. Paul, Minn. For added benefits, the phase-change liquid may include a skin wellness agent, such as a medicant, emollient, ointment, moisturizer, and the like.

It may be desired in certain embodiments that the deposit substance incorporate a highly visible color. In this manner, the deposit substance may be applied in a visible and pleasing aesthetic pattern.

For description purposes only, the barrier substance deposits will be referred to from this point with reference to the phase-change liquid embodiment thereof. It should be appreciated that the invention is not, however, limited to phase-change liquids, but encompasses any substance that can be deposited onto a material in a pattern so as to define the discrete barrier topographies as described herein.

The deposits 32 of the phase-change liquid may be applied to the top cover 12 by various techniques. For example, the phase-change liquid may be deposited by use of a piezo-driven print head. The piezo-driven print devices are typically capable of emitting droplets having a diameter in the range of about 50-90 micrometers with placement resolution to about 1/200 of an inch. The phase-change liquid may be deposited in a single or multiple pass of the top cover 12 past the print head, or multiple print heads may be used. In an alternate desirable embodiment, the phase-change liquid is deposited by an inkjet printing technique. Suitable inkjet printing techniques are described, for example, in co-pending U.S. patent application Ser. No. 09/990,686 filed on Nov. 16, 2001, and entitled "MATERIAL HAVING ONE OR MORE CHEMISTRIES WHICH PRODUCE TOPOGRAPHY, UNIQUE FLUID HANDLING PROPERTIES AND/OR BONDING PROPERTIES THEREON AND/OR THEREIN" and U.S. patent application Ser. No. 09/991,185 filed on Nov. 16, 2001, and entitled "APPARATUS AND METHOD TO PRODUCE TOPOGRAPHY, UNIQUE FLUID HANDLING PROPERTIES AND BONDING PROPERTIES ON OR WITHIN SUBSTRATES." These co-pending applications are incorporated herein by reference for all purposes.

The phase-change liquid is applied at add-on levels of between about 0.5 gsm (grams per square meter) to about 13.0 gsm, desirably less than about 10 gsm, and more desirably between about 2.0 gsm to about 5.0 gsm.

Referring to FIGS. 1 and 2, it can be seen that the article 10 may include two longitudinally extending bands 30 of phase-change liquid deposits 32. In this particular embodiment, the bands 30 are defined by relatively thin, parallel, and continuous stripes extending longitudinally on opposite sides of a centerline axis of the article 10. In this particular embodiment, the bands 30 are defined by laterally outboard stripes 34 and laterally inboard stripes 36. The laterally outboard stripes 34 may be generally coextensive with an outer periphery of the underlying absorbent structure 18. Thus, in this embodiment, the band completely overlies longitudinal periphery portions or edges of the underlying absorbent structure 18. The bands 30 may extend completely between the longitudinal ends 22 of the article 10, as depicted in FIG. 1. In an alternate embodiment as illustrated in FIG. 3, the parallel deposit stripes 32 extend laterally outboard to the sealed periphery edges 16 of the article 10.

The individual deposits 32, particularly in the stripe configuration of FIGS. 1 through 3, may have an individual width of about 0.25 mm and be spaced apart by at least the width of one stripe, and desirably at least three stripes. For example, an exposed area of about 0.75 mm may be defined between each parallel stripe, with the band having an overall transverse width between about 5 mm to about 20 mm, preferably between 8 mm to about 14 mm, along the portion overlying the absorbent structure 18. For example, referring to FIG. 1, the width between the laterally outboard stripe 34 and laterally inboard strip 36 may be between about 5 mm to about 20 mm. Referring to FIG. 3, the transverse width of the band 30 between the laterally inboard stripe 36 to the sealed edges 16 of the article 10 may vary and be substantially greater than 20 mm. However, the portion of the band 30 overlying the absorbent structure 18 may be between about 5 mm to about 20 mm, for example from about 8 mm to about 14 mm. It should be appreciated that the transverse width dimension is not a limiting factor of the invention and various widths are contemplated and may be empirically determined to provide the benefits of preventing leakage of bodily fluids at the lateral sides 20 of the article 10 while still allowing for absorption of bodily fluids deposited over the bands 30.

Figure 8:
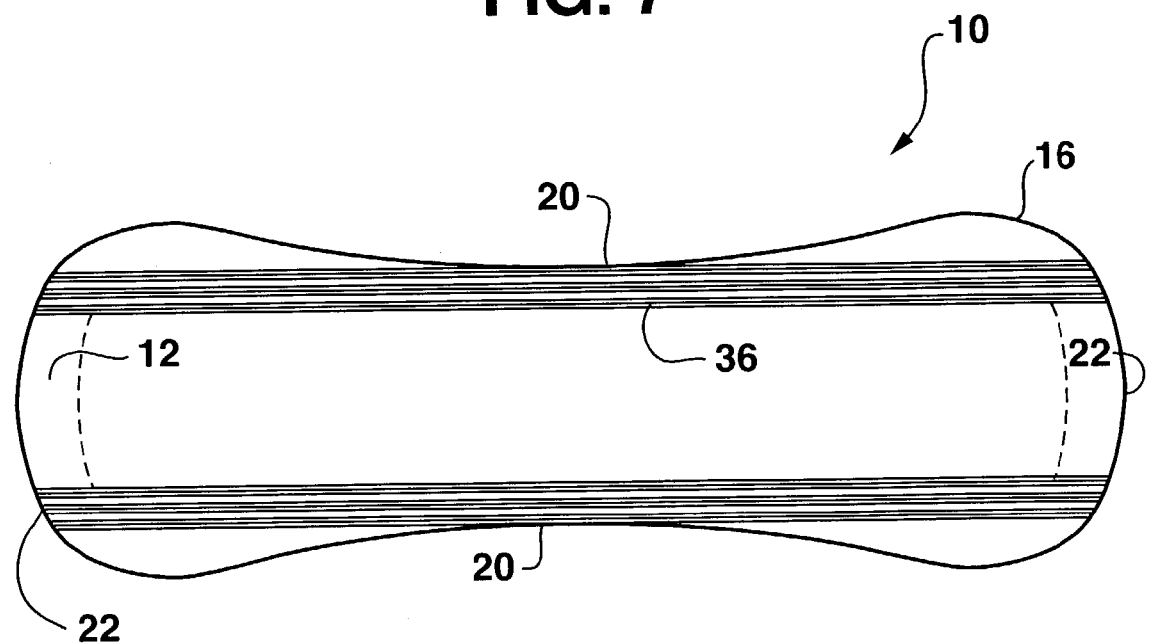
FIG. 8 is a top plan view of an alternate embodiment of the invention.

FIG. 8 illustrates another type of band pattern in accordance with the invention. In this embodiment, sets of multiple closely spaced stripe deposits are spaced apart a distance of between about 0.25 mm to about 0.75 mm between each set. Each set may contain any number of stripes so long as the desired percentage of uncovered area of liner is maintained between the laterally outboard and laterally inboard sets of stripes.

Figure 4:
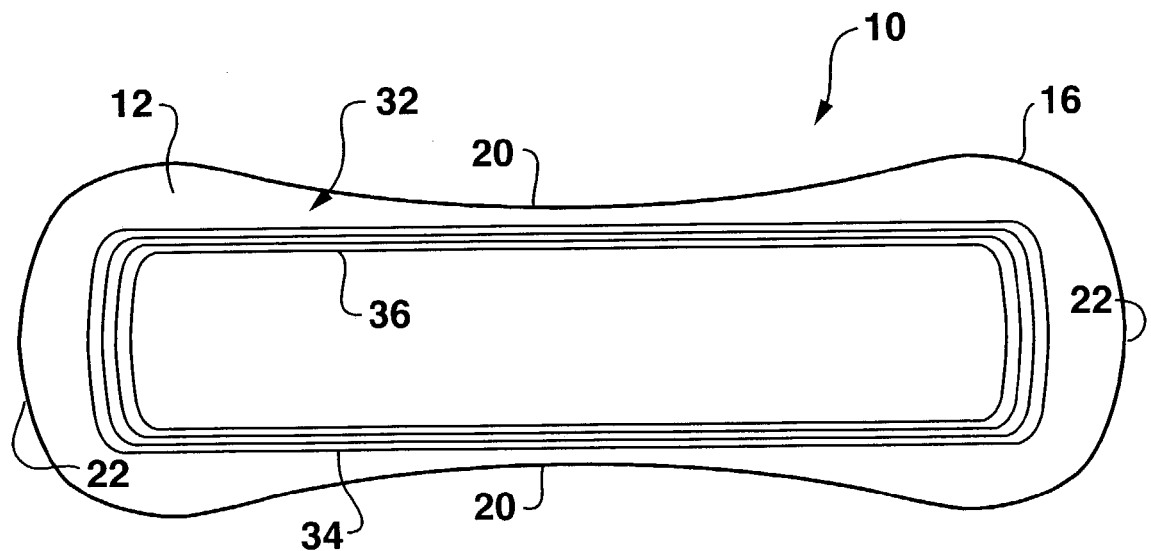
FIG. 4 is a top plan view of an alternate embodiment of the invention.

FIG. 4 illustrates an alternate embodiment wherein the band 30 is defined generally around a complete periphery of the article 10. As mentioned, although the focus of leakage from such articles 10 is generally along the lateral sides 20 of the article, leakage can also occur at the longitudinal ends 22. The embodiment of FIG. 4 may address this problem. It should also be appreciated that, although the band 30 is illustrated in FIG. 4 as having a laterally outboard deposit 34 spaced from the peripheral sealed edge 16 of the article 10, the stripes 32 may just as well extend laterally outboard to the sealed edge 16.

Figure 5:
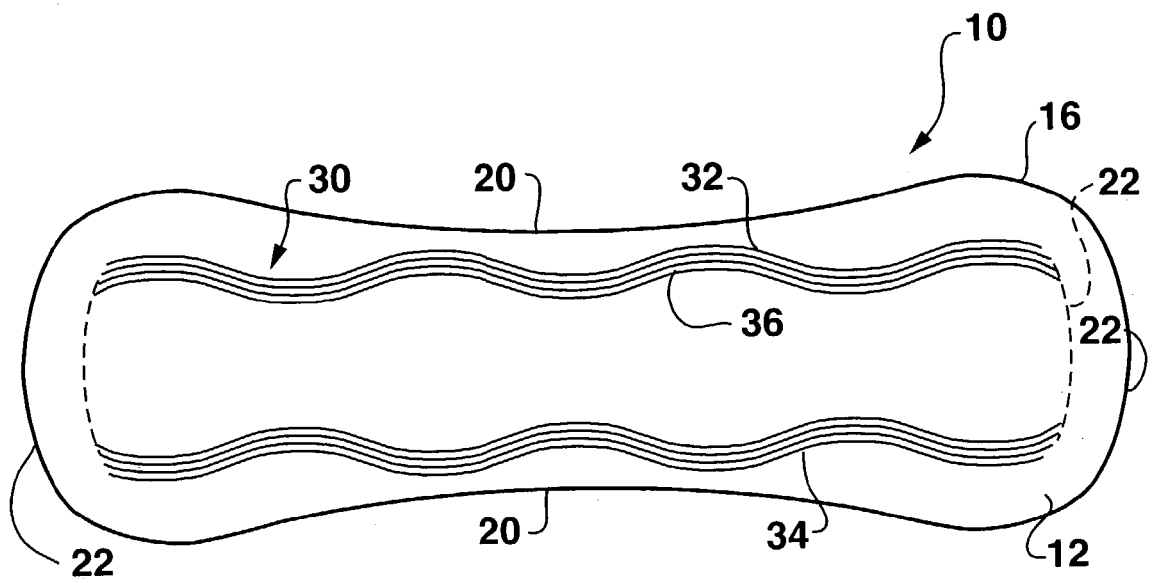
FIG. 5 is a top plan view of an alternate embodiment of the invention.

FIG. 5 illustrates an alternate embodiment wherein the bands 30 are defined by generally parallel and sinusoidal or wave-like deposits 32. The deposits 32 do not extend in this embodiment to the longitudinal ends 22 of the article 10, as compared to the embodiment of, for example, FIGS. 1 and 3.

Figure 6:
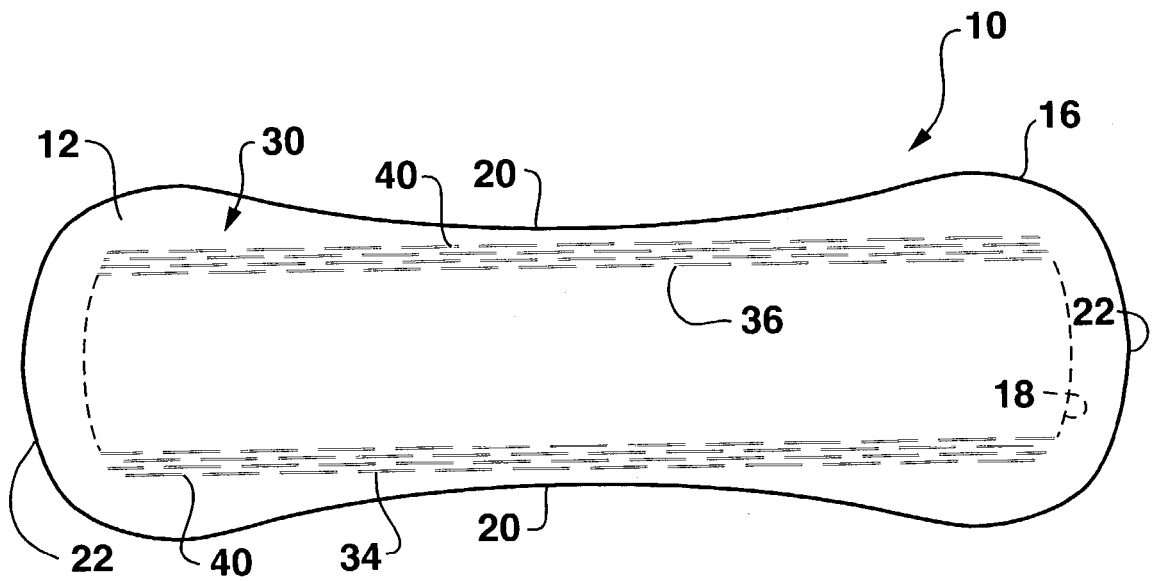
FIG. 6 is a top plan view of an alternate embodiment of the invention.
Figure 7:
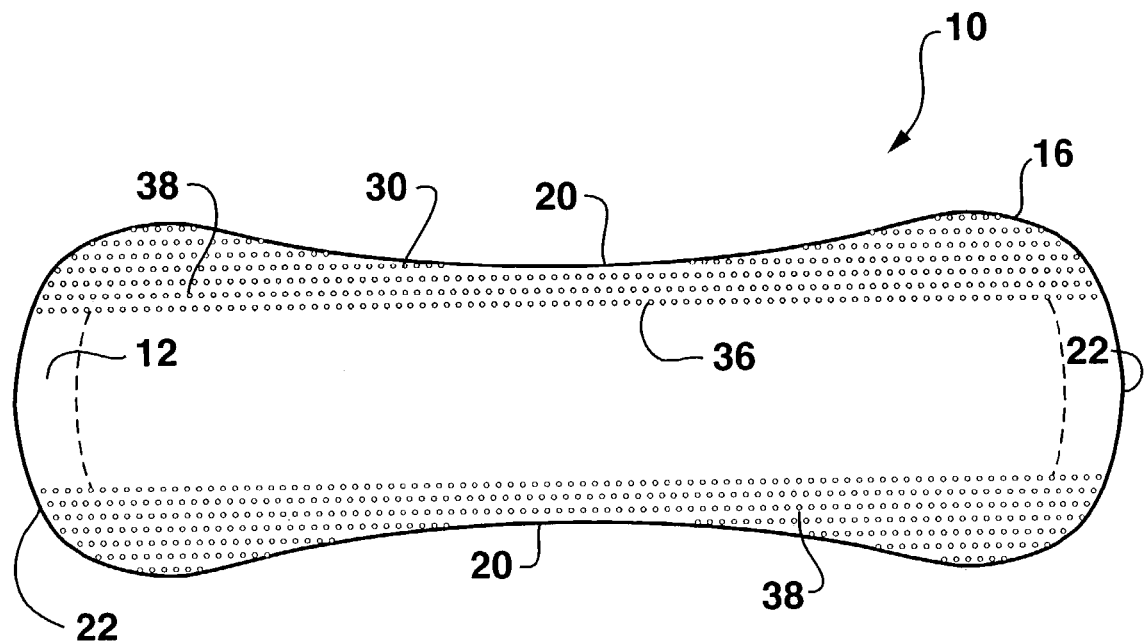
FIG. 7 is a top plan view of an alternate embodiment of the invention.

FIG. 6 illustrates an embodiment wherein the bands 30 are defined by discontinuous deposits of the phase-change liquid. In this particular embodiment, the band 30 is defined by parallel dashed lines 40. It may be desired that the dashes 40 of the different individual parallel lines be interspaced such that a tortuous path is defined between the laterally inboard deposits 36 and laterally outboard deposits 34. In this manner, bodily fluids migrating laterally outboard are not provided with a clear unimpeded path to the lateral sides 20 of the article 10, but are caused to change directions numerous times before reaching the edges 16 of the article. A discontinuous path as illustrated in FIG. 6 may be desired in that the bodily fluids are directed between the deposits 32 to unexposed areas within the band, as compared to the embodiment of, for example, FIGS. 1 and 3, wherein bodily fluids migrating laterally outward along the top cover 12 would need to flow over the individual deposits 32 before being absorbed between the individual stripes.

FIG. 7 illustrates an alternative embodiment of a discontinuous pattern for the bands 30. In this embodiment, the deposits are defined by individual drop-like deposits 38 that, upon solidification, form individual dome-shaped barriers on the top cover 12. As described above with reference to FIG. 6, the dome deposits are interspaced so that bodily fluids migrating laterally outward from a center portion of the article 10 are directed to the exposed areas between the dome structures 38.

It should be appreciated that numerous pattern variations are contemplated for the bands 30 of phase-change liquid. The embodiments illustrated in the figures are for exemplary purposes only. The invention includes any suitable band pattern exposing a sufficient portion of the top cover 12 for absorption of bodily fluids that are deposited from above the bands.

It should be appreciated by those skilled in the art that various modifications and variations can be made to the embodiments of the absorbent article described herein without departing from the scope and spirit of the invention as set forth in the appended claims and equivalents thereof.

What is claimed is:

1. An absorbent article, comprising:
    a liquid permeable top cover;
    a generally liquid impermeable outer cover;
    an absorbent structure disposed between said top cover and said outer cover;
    spaced apart continuous deposits of a barrier substance material defined on said top cover in longitudinally extending bands on opposite sides of a longitudinal centerline of said article, at least a portion of said longitudinally continuous bands overlying longitudinal periphery portions of said underlying absorbent structure, each said longitudinally continuous band comprising a plurality of said continuous deposits of said barrier substance including a laterally inboard continuous deposit and a laterally outboard continuous deposit, said portion of said longitudinally continuous bands overlying said absorbent structure being between about 5 mm to about 20 mm, wherein said laterally inboard and laterally outboard spaced apart continuous deposits are spaced apart a distance of from about 0.25 to about 0.75 mm, said longitudinally continuous bands comprising the only deposits of barrier substance material present on said top cover; and
    wherein the total surface area portion of said top cover is encompassed within the periphery of said top cover, and the total exposed surface area portion of said top cover is encompassed between said laterally outboard and laterally inboard continuous deposits and between said longitudinally continuous bands said longitudinally continuous bands thus acting as a fluid barrier against lateral flow of bodily fluids across said longitudinally continuous bands and being generally permeable to bodily exudates insulting said article from generally above said longitudinally continuous bands.

2. The absorbent article as in claim 1, wherein said article comprises a feminine care absorbent article.

3. The absorbent article as in claim 2, wherein said article is a sanitary napkin.

4. The absorbent article as in claim 1, wherein said laterally outboard continuous deposit is disposed over said absorbent structure generally coextensive with said periphery of said underlying absorbent article.

5. The absorbent article as in claim 1, wherein said bands extend around less than all of a periphery of said article.

6. The absorbent article as in claim 1, wherein said bands extend around an entirety of a periphery of said article.

7. The absorbent article as in claim 1, wherein the barrier substance material comprises a phase-change liquid.

8. The absorbent article as in claim 7, wherein said phase-change liquid is any combination of a wax, petrolatum based lotion, adhesive, and thermoplastic.

9. The absorbent article as in claim 7, wherein said phase-change liquid comprises a skin wellness additive.

10. The absorbent article as in claim 1, wherein said spaced apart continuous deposits comprise generally parallel stripes.

11. The absorbent article as in claim 10, wherein said stripes have a width of about 0.25 mm.

12. The absorbent article as in claim 1, wherein said bands have a transverse width between said laterally outboard and said laterally inboard continuous deposits of between about 5 mm to about 20 mm.

13. A feminine care absorbent article, comprising:
    a liquid permeable top cover;
    a generally liquid impermeable outer cover;
    an absorbent structure disposed between said top cover and said outer cover;
    a band of spaced apart solidified deposits of a phase-change liquid defined on said top cover along a portion of opposite lateral sides of said article, said deposits having a desired height with respect to a bodyfacing surface of said top cover;
    said bands comprising a series of spaced apart and generally parallel continuous deposits of said phase change liquid having a laterally inboard continuous deposit and a laterally outboard continuous deposit, a portion of said generally parallel continuous bands overlying said absorbent structure being between about 5 mm to about 20 mm, wherein said spaced apart and generally parallel continuous deposits are spaced apart a distance of from about 0.25 to about 0.75 mm, said generally parallel continuous bands comprising the only deposits of phase change liquid present on said top cover; and
    wherein the total surface area portion of said top cover is encompassed within the periphery of said top cover, and the total exposed surface area portion of said top cover is encompassed between said laterally outboard and laterally inboard continuous deposits and between said generally parallel continuous bands thus acting as a fluid barrier against lateral flow of bodily fluids across said generally parallel continuous bands and being generally permeable to bodily exudates insulting said article from generally above said generally parallel continuous bands.

14. The feminine care absorbent article as in claim 13, wherein said phase-change liquid is any combination of a wax, petrolatum based lotion, adhesive, and thermoplastic.

15. The feminine care absorbent article as in claim 13, wherein said spaced apart continuous deposits comprise generally parallel stripes.

16. The feminine care absorbent article as in claim 15, wherein said stripes have a width of about 0.25 mm.

* * * * *